United States Patent
Bertram et al.

(10) Patent No.: US 7,392,813 B2
(45) Date of Patent: Jul. 1, 2008

(54) DEVICE FOR A TURBIDITY SENSOR FOR A DISHWASHER OR WASHING MACHINE

(75) Inventors: Andre Bertram, Bielefeld (DE); Erik Berends, Bielefeld (DE); Michael Reilmann, Bielefeld (DE)

(73) Assignee: Miele & Cie. KG, Guetersloh (DE)

( * ) Notice: Subject to any disclaimer, the term of this patent is extended or adjusted under 35 U.S.C. 154(b) by 534 days.

(21) Appl. No.: 10/833,647

(22) Filed: Apr. 28, 2004

(65) Prior Publication Data

US 2004/0216774 A1 Nov. 4, 2004

(30) Foreign Application Priority Data

Apr. 29, 2003 (DE) ................ 103 19 467

(51) Int. Cl.
 *D06F 33/00* (2006.01)
 *B08B 3/00* (2006.01)
 *A47L 15/42* (2006.01)

(52) U.S. Cl. .............. 134/56 D; 134/57 D; 134/113; 68/12.02

(58) Field of Classification Search ........... 134/56 D
 See application file for complete search history.

(56) References Cited

U.S. PATENT DOCUMENTS

| 4,690,560 A | * | 9/1987 | Coogan | ............ 356/338 |
| 5,331,177 A | * | 7/1994 | Kubisiak et al. | ............ 250/574 |
| 5,586,567 A | * | 12/1996 | Smith et al. | ............ 134/57 D |
| 2002/0062849 A1 | * | 5/2002 | Ekelhoff | ............ 134/113 |

FOREIGN PATENT DOCUMENTS

| DE | 10059112 | | 5/2002 |
| DE | 10146641 | | 12/2002 |
| DE | 10146641 C1 | * | 12/2002 |
| EP | 1092384 | | 4/2001 |
| EP | 1208790 | | 5/2002 |
| GB | 1469189 | | 3/1977 |
| JP | 05154278 | * | 6/1993 |

* cited by examiner

*Primary Examiner*—Michael Barr
*Assistant Examiner*—Jason P Riggleman
(74) *Attorney, Agent, or Firm*—Darby & Darby

(57) ABSTRACT

A device for preventing foam or air bubbles from accumulating in a measuring zone of a turbidity sensor connected in a wash-water circuit of a dishwasher or washing machine includes a main flow conduit and a bypass conduit connected to the main flow conduit. The bypass conduit includes a first conduit section branching off from the main flow conduit, a second conduit section leading back into the main flow conduit at a junction, and an enlarged region of reduced flow velocity connected upstream of the junction. The enlarged region provides the measuring zone for the turbidity sensor, and includes a curved baffle and a downward-facing bulbous protuberance opposite the baffle so as to form a backflow region. The measuring zone is located within the backflow region in the bulbous protuberance.

20 Claims, 2 Drawing Sheets

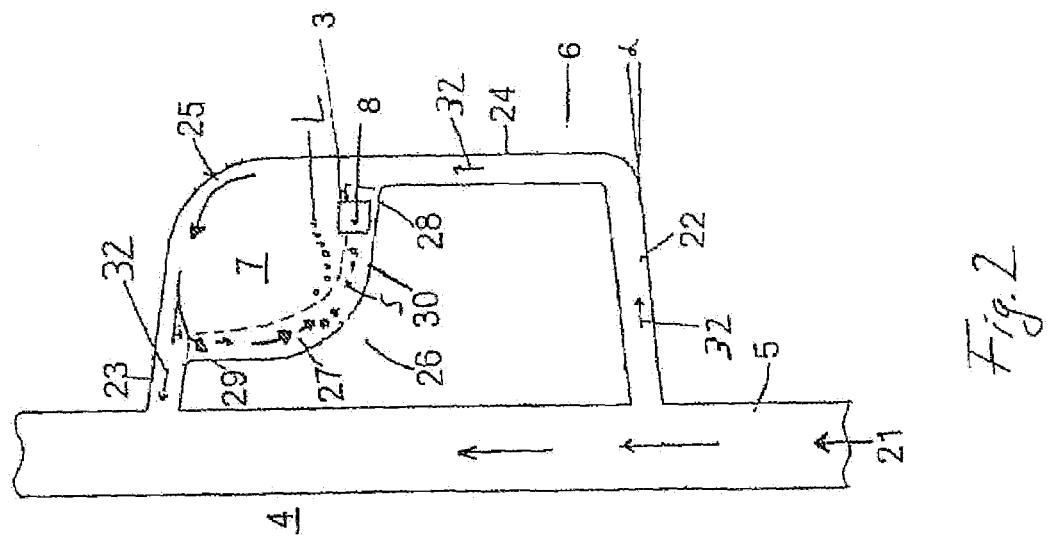
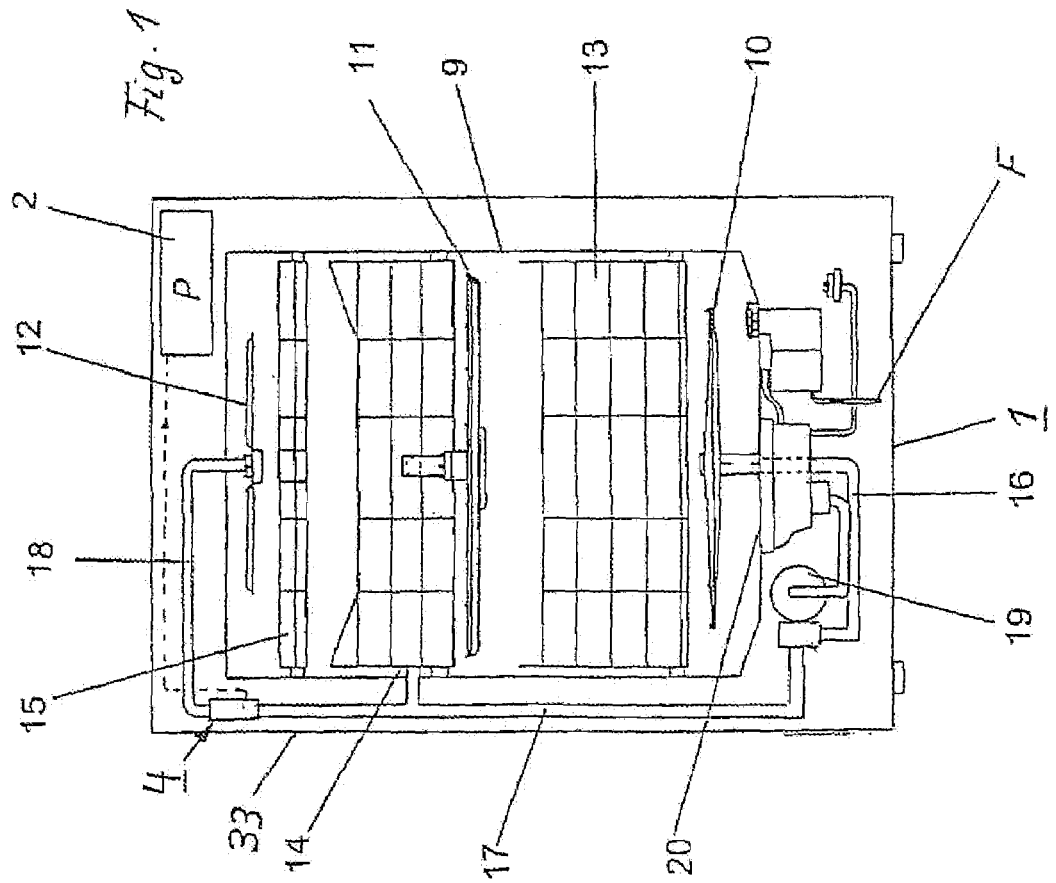

DEVICE FOR A TURBIDITY SENSOR FOR A DISHWASHER OR WASHING MACHINE

Priority is claimed to German patent application DE 103 19 467.3, the subject matter of which is hereby incorporated by reference herein.

The present invention relates to a device for preventing foam or air bubbles from accumulating in the measuring zone of a turbidity sensor located in the wash-water circuit of a dishwasher or washing machine, the device including a main flow conduit and, connected thereto, a bypass conduit having a first conduit section branching off from the main flow conduit, a second conduit section leading back into the main flow conduit, and an enlarged region of reduced flow velocity upstream of the junction as a measuring zone for the turbidity sensor.

BACKGROUND

In modern, water-using household appliances, in particular, in program-controlled dishwashers, turbidity sensors are used to optimize the wash-program sequence. Ideally, during a measuring interval, a turbidity sensor which, in particular, is configured with optical means sends signals to an evaluation device provided in the appliance, these signals including signals representative of the degree of discoloration or of the transparency of the wash water as well as signals representative of the number of dirt particles detected in the wash water during the measuring interval. Based on the degree of discoloration and the number of dirt particles, the evaluation device then calculates the degree of turbidity which, in turn, influences the program sequence of the appliance. However, in practice, it turned out that the measuring zone of the turbidity sensor is also traversed by air bubbles and foam. However, the turbidity sensor cannot differentiate between air bubbles and dirt particles. Therefore, the turbidity sensor sends faulty signals for the number of dirt particles to the evaluation device, making it more difficult to calculate an exact degree of turbidity. A comparable problem occurs in washing machines when foam bubbles increasingly accumulate in the washing liquid.

In the earlier German Patent DE 100 59 112 C1, the applicant proposed to solve these problems by moving the circulating wash water at a reduced flow velocity within a measuring zone. In this connection, the measuring zone, together with the turbidity sensor, is disposed in a horizontally extending wash water conduit section which continuously widens upward with respect to the horizontal plane and forms a stilling section for the fluid flow. In the space of reduced flow velocity, it is possible for air bubbles to accumulate in a plane above the measuring zone and to be removed with the flow.

However, this approach was found to have the disadvantage that when the circulating pump moving the wash water operates at full flow, the dwell time of the wash water in the stilling section is very short so that there are still some air bubbles and foam passing through the measuring zone.

In German Patent DE 101 46 641 C1, the applicant proposed to solve the problem by a device having a main flow conduit and a parallel bypass conduit which is connected to the main flow conduit and features an enlarged region of reduced flow velocity in which is located the measuring zone for the turbidity sensor.

This was an improvement over the prior art described earlier, but tests have shown that, occasionally, there are still air bubbles traversing the measuring zone during the washing operation.

SUMMARY OF THE INVENTION

It is an object of the present invention to provide a device having a measuring zone for a turbidity sensor in a bypass conduit in such a manner that during the washing operation, the measuring zone is traversed by bubble-free wash water and the dirt particles contained therein.

The present invention provides a device for preventing foam or air bubbles from accumulating in the measuring zone of a turbidity sensor located in the wash-water circuit of a dishwasher or washing machine. The device includes a main flow conduit and, connected thereto, a bypass conduit having a first conduit section branching off from the main flow conduit, a second conduit section leading back into the main flow conduit, and an enlarged region of reduced flow velocity upstream of the junction as a measuring zone for the turbidity sensor. The region of reduced flow velocity is configured with a curved baffle in the bypass conduit, and a downward-facing bulbous protuberance which is located on the opposite wall side within this conduit section and serves to form a backflow region; the measuring zone being located within the backflow region in the bulbous protuberance.

The baffle deflects part of the wash-water flow into a circular path so that a slow backflow forms in the downward-facing bulbous protuberance. Due to circular motion, the air bubbles are caused to rise upward because of their density before they reach the measuring zone, while the dirt particles contained in the wash water pass through the measuring zone with the backflow due to gravity.

In addition to optimized separation of air bubbles from the wash water upstream of the measuring zone of the turbidity sensor, a particular advantage that can be achieved with the present invention is that the flow velocity of the wash water in the region of the measuring zone is so low that the wash water, together with the dirt particles contained therein, passes through the measuring zone of the turbidity sensor located in the backflow region very slowly compared to the prior art, which allows the use of a turbidity sensor having a low sampling rate and a slow processor for evaluating the turbidity levels. Furthermore, in this manner, noisy turbidity signals caused by a quick succession of dirt particles are reliably avoided.

In an embodiment of the present invention, it is proposed that upstream of the region of reduced flow velocity, the bypass conduit is aligned such that it extends upright. In this manner, the wash water entering the enlarged region of reduced flow velocity fans out widely so that the wash-water pressure produced by the circulating pump decreases and the flow velocity of the wash water is reduced. In another embodiment of the present invention, the region of reduced flow velocity is bounded in the main flow direction of the bypass conduit by an abrupt enlargement and an abrupt narrowing of the bypass conduit to further reduce the flow velocity.

According to an embodiment of the present invention, the bulbous protuberance is formed in a bypass wall section facing the main flow conduit. In this embodiment, the enlarged region of reduced flow velocity extends into the space between the bypass conduit and the main flow conduit. This allows the device to be designed as a small component requiring little space.

In an embodiment of the present invention, the device is designed as a flat component, enabling the bypass conduit to be inserted nearly anywhere in a dishwasher or washing machine. Thus, in a dishwasher having a housing side wall and a washing tub, the device can even be mounted in the narrow gap between a housing wall and the washing tub.

Accordingly, in another embodiment of the present invention, it is proposed for the device to be disposed in the flow path of a spray arm conduit fed by a circulating pump with the main flow conduit of the device being aligned vertically. Due to this configuration, the device is easy to access, especially when compared to the standard location in the packed base region, allowing quick and inexpensive installation and replacement in case of servicing. To further add to the ease of replacement of the unit, in a further embodiment of the present invention, the device is disposed between the housing side wall and the washing tub and is replaceably, i.e., detachably connected to the spray arm conduit. An alternative would be a one-piece design of the device and the spray arm conduit. Thus, in particular, the high installation cost for the device is eliminated.

In an embodiment of the present invention, the main flow conduit is arranged at least 40 cm above the circulating pump. At this height, the swirl components produced by the circulating pump are already strongly reduced.

In an embodiment of the present invention, the baffle in the main flow direction of the bypass conduit leads into the second conduit section that leads back into the main flow conduit.

In an embodiment of the present invention, the abrupt enlargement is slightly inclined downwardly in the direction of the backflow and with respect to a horizontal plane, preferably at an angle of inclination between 10° and 20°. Since when the circulating pump is turned off, a backflow forms in the bypass conduit due to gravity, the aforementioned embodiment has the advantage that dirt particles that have accumulated in the bypass conduit are reliably washed out of the bypass conduit and into the main flow conduit with the backflow. From there, the dirt particles are transported into the washing tub during the next washing operation by the full washing pressure produced by the circulating pump. This prevents adherence of the dirt particles in the bypass conduit even when the appliance is not used for a prolonged period. For the mentioned reasons, in an embodiment of the present invention, the first conduit section and the second conduit section are slightly inclined downwardly with respect to a horizontal plane in a direction opposite to the main flow direction of the bypass line, preferably at an angle of inclination between 10° and 20°.

The present invention is in an embodiment useable in an electronically programmable dishwasher, whose manually or automatically selectable wash programs each include separate program cycles, such as pre-rinse, main wash, intermediate rinse, and final rinse; the pre-rinse and/or intermediate rinse cylces being able to be eliminated or added depending on the detected soil level of the loaded dishes. The final rinse cycle is usually followed by a drying cycle. Dishwashers of this type are well-known in the art.

BRIEF DESCRIPTION OF THE DRAWINGS

An exemplary embodiment of the present invention is shown in the drawings schematically and will be described in more detail below.

FIG. 1 shows a sectional view of program-controlled dishwasher with a simplified representation of its components and accessories, a device having a measuring zone for a turbidity sensor being provided in the water circuit of the appliance for determining the degree of turbidity of the wash water.

FIG. 2 shows an enlarged longitudinal sectional view of the device of FIG. 1.

DETAILED DESCRIPTION

Figure 3:
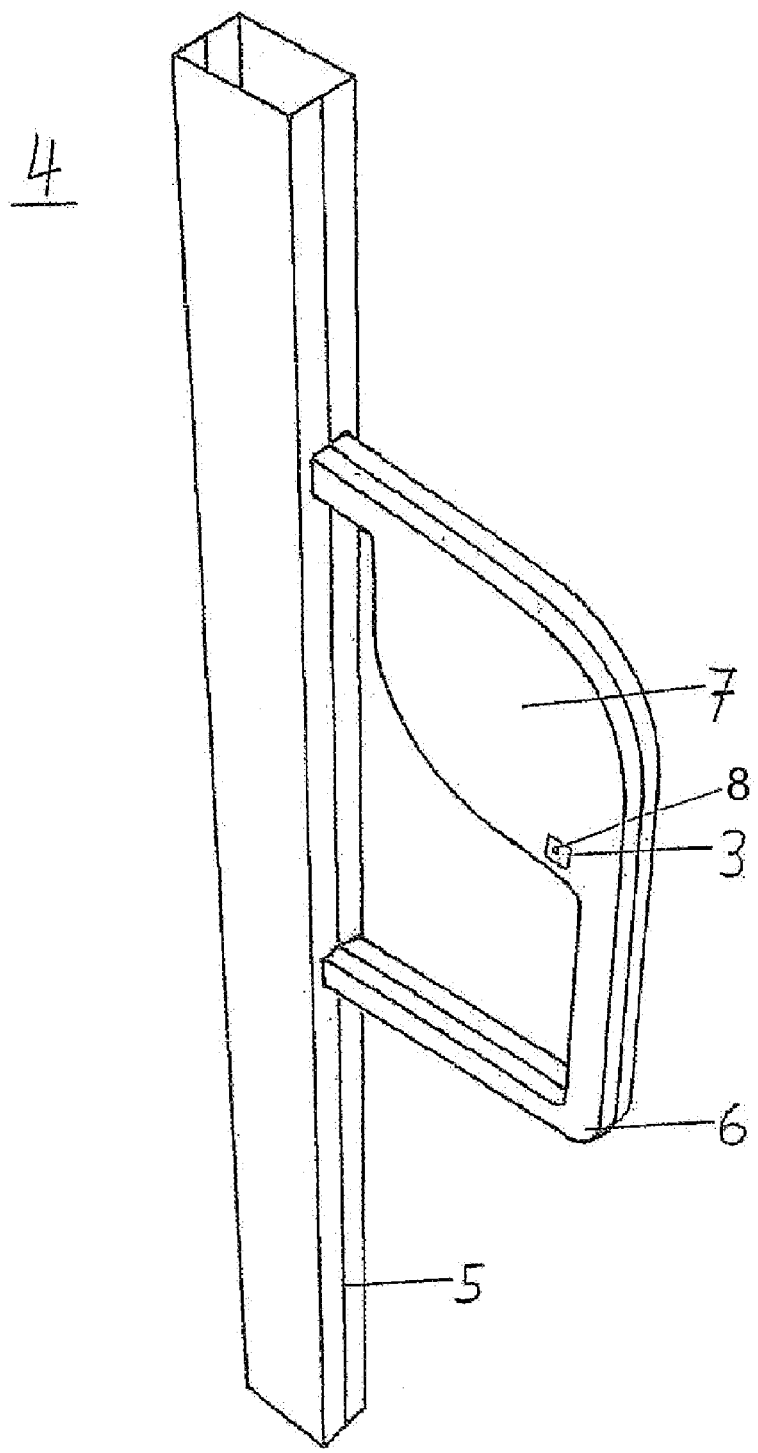
FIG. 3 shows the device of FIG. 2 in a perspective view.

A household dishwasher 1 is shown in FIG. 1. The program control module 2 of the appliance has been shown schematically only; a detailed illustration is not shown for the sake of clarity. In order to optimize the wash-program sequence, a dishwasher designed in this manner can be equipped with a turbidity sensor 3 (see FIG. 2) that detects wash-water turbidities during the water-using program steps. In this connection, it is important for the air bubbles or foam components carried in the wash water not to corrupt the measurement result. Therefore, as will be described in more detail below, there is provided a device 4 including a main flow conduit 5 and, connected thereto, a bypass conduit 6 which is designed as a bubble trap and has a region of reduced flow velocity 7 for the measuring zone 8 of turbidity sensor 3.

Front-loading dishwasher 1 has a washing tub 9 and several spray arms 10, 11, 12 arranged in different planes in washing tub 9 above and between dish racks 13, 14 and a separate cutlery tray 15. Spray arms 10 through 12 are supplied with circulating wash water 21 by way of associated spray arm conduits 16 through 18 from a circulating pump 19 arranged upstream in the base region. In the present embodiment, spray arm conduit 17 feeds both the middle spray arm 11 and the upper spray arm 12. During the washing operation, the wash water 21 accumulating in the bottom region of washing tub 9 is constantly circulated through a filter combination 20 composed of a very fine filter and a coarse filter to filter out food remains, and fed to spray arms 10 through 12 via the spray arm conduits 16 through 18 arranged downstream of circulating pump 19. A connection for the fresh water to be supplied to the appliance is denoted by F.

Device 4, which is shown in more detail in FIG. 2 and, according to FIG. 3, has a flat shape, is arranged with its main flow conduit 5 in the vertical flow path of spray arm conduit 17 so that during the washing operation, wash water 21 passes through main flow conduit 5 from the bottom to the top. In order to reduce the vortices and swirl components produced by circulating pump 19, device 4 is located in a section of spray arm conduit 17 far above circulating pump 19, preferably 50 cm above circulating pump 19 at the level of upper spray arm 12, between a housing side wall 33 and washing tub 9.

According to FIGS. 2 and 3, bypass conduit 6 is connected to the vertically extending main flow conduit 5 of device 4, the bypass conduit having a first conduit section 22 branching off from the main flow conduit 5, a second conduit section 23 leading back into the main flow conduit 5, and a region of reduced flow velocity 7 for the measuring zone 8 of turbidity sensor 8. According to the embodiment of FIGS. 2 and 3, bypass conduit 6 has an approximately U-shaped configuration as seen in the longitudinal section, and has a middle conduit section 24.

In principle, however, middle conduit section 24 is not necessarily required for the bypass conduit 6 according to the present invention.

The region of reduced flow velocity 7 is configured with a curved, for example an at least nearly radial (circular), baffle 25 in bypass conduit 6, and a bulbous protuberance 26 which is located on the opposite wall side 30 within this conduit section 22, 23 and faces downward toward the base region, and which serves to form a backflow region 27 shown in dashed lines in FIG. 2. Accordingly, the backflow is due to both radial baffle 25 and bulbous protuberance 26. According to FIG. 2, radial baffle 25 is preferably located between conduit sections 23, 24.

The measuring zone 8 for turbidity sensor 3 is provided within backflow region 27, because here the wash water 21, on the one hand, contains the dirt particles S that are characteristic for the turbidity measurement, but, on the other hand, and especially at the end of the backflow path, the wash water is free of the air bubbles L that may lead to corruption of turbidity measurements. In order for backflow region 27 to be optimally configured, which will be described in more detail below, the region of reduced flow velocity 7 is bounded by an abrupt enlargement 28 and an abrupt narrowing 29.

Bulbous protuberance 26 is formed in a bypass wall section 30 facing the main flow conduit 5, as shown in FIGS. 2 and 3. This bypass wall section bends toward the main flow conduit 5 upstream of baffle 25 in the main flow direction 32 of bypass conduit 6, which is indicated by arrows, and, via a circular section and a section facing upward in a nearly vertical direction, connects to a wall section of the nearly horizontally extending conduit section 23. In this connection, the bend of bypass wall section 30 forms the enlargement 28 while the narrowing 29 bounding the region of reduced flow velocity 7 is formed by the portion of wall section 30 that leads vertically upward and is nearly perpendicular to conduit section 23.

The above-described configuration of the enlarged region of reduced flow velocity 7 results in the formation of the backflow region 27 within the region of reduced flow velocity 7 as indicated in FIG. 2 and described below.

When wash water 21 enters the enlarged region of reduced flow velocity 7, the wash-water pressure produced by the circulating pump 19 and the flow velocity are reduced. In the process, the flow component of wash water 21 flowing on the side of enlargement 28 fans out within the region of reduced flow velocity 7 due to the abrupt, unilateral enlargement 28. The flow component of wash water 21 flowing on the side of baffle 25 flows along the radially extending baffle 25 toward the narrowing 29 of bypass conduit 6; the radially extending baffle 25 imparting a swirl component to the volume flow, forcing it into a circular path of motion which is directed toward the enlargement 28 and marked by arrows in FIG. 2. At the narrowing 29 of bypass conduit 6, a backflow toward the enlargement 28 is formed due to this circular path, the backflow moving mainly along bypass wall section 30 at a very low flow velocity. As a result of the low backflow velocity and the circular section of bypass wall section 30 between the enlargement 28 and the narrowing 29, air bubbles L that are still contained in the volume flow of wash water 21 are caused to rise upward in a defined manner as shown in FIG. 2 while dirt particles S carried in wash water 21 move with the backflow along bypass wall 30 due to the attraction of gravity. Therefore, for measuring dirt particles S and the turbidity of a bubble-free wash fluid 21, the measuring zone 8 is arranged in backflow region 27 near bypass wall section 30. Since, of course, more and more air bubbles L escape with increasing backflow length, the measuring zone 8 for turbidity sensor 3 is arranged at the end of backflow region 27 that is bounded by enlargement 28.

In the exemplary embodiment according to FIGS. 2 and 3, it is proposed that the enlargement 28 be slightly inclined downwardly in the direction of the backflow with respect to the horizontal plane, and that conduit sections 22, 23 be slightly inclined downwardly with respect to the horizontal plane in a direction opposite to main flow direction 32 so that when the circulating pump is turned off, the dirt particles S carried into bypass conduit 6 from wash water 21 are reliably transported into main flow conduit 5 with the backflow occurring in the whole bypass conduit due to gravity. During the washing operation, the particles S are, for the most part, transported with wash water 21 from main flow conduit 5 into the wash chamber, from where they are transported with wash water 21 into a sink by a drain pump in a manner known per se. Particularly good results were obtained when the aforementioned bypass walls 22, 23, 28 were at an angle of inclination α of 10° to 20° with respect to the horizontal plane (see FIG. 2).

What is claimed is:

1. A washing device comprising:
   a main flow conduit that is vertically disposed in an operating position of the washing device; and
   an apparatus for preventing foam or air bubbles from accumulating in a measuring zone of a turbidity sensor connected in a wash-water circuit of the washing device, the apparatus comprising
   a bypass conduit connected to the main flow conduit, the bypass conduit including:
   a first conduit section branching off from the main flow conduit at a branching off location;
   a second conduit section leading back into the main flow conduit at a junction vertically above the branching off location; and
   an enlarged region of reduced flow velocity connected between the first and second conduit sections and providing the measuring zone of the turbidity sensor, the enlarged region including an abrupt enlargement and an abrupt narrowing of the bypass conduit forming a curved baffle and a downward-facing bulbous protuberance opposite the baffle so as to form a backflow region, the measuring zone being disposed in the backflow region in the bulbous protuberance.

2. The device as recited in claim 1 wherein a side wall of the bypass conduit forms the bulbous protuberance.

3. The device as recited in claim 1 wherein the bypass conduit includes a middle conduit section connected upstream of the enlarged region, the middle conduit section configured to convey flow in a vertical direction relative to a direction of gravity.

4. The device as recited in claim 1 wherein a wall portion of the bypass conduit disposed opposite the main flow conduit forms the bulbous protuberance.

5. The device as recited in claim 1 wherein the baffle directs flow, in a main flow direction of the bypass conduit, into the second conduit section.

6. The device as recited in claim 1 wherein a portion of the abrupt enlargement is downwardly, relative to a direction of gravity, inclined with respect to a horizontal plane in a direction of backflow.

7. The device as recited in claim 6 wherein the portion of the abrupt enlargement is downwardly inclined at an angle of inclination of between 10° and 20° with respect to the horizontal plane.

8. The device as recited in claim 1 wherein the first conduit section and the second conduit section are each upwardly inclined, relative to a direction of gravity, with respect to a horizontal plane in a respective direction of flow in the respective conduit section.

9. The device as recited in claim 8 wherein the first conduit section and the second conduit section are inclined upwardly at an angle of inclination of between 10° and 20° with respect to the horizontal plane.

10. The device as recited in claim 1 wherein the device has a flattened shape.

11. The device as recited in claim 1 wherein the bypass conduit includes a middle conduit section connected between the first conduit section and the second conduit section, the bypass conduit having a substantial U-shape.

12. The device as recited in claim 1 wherein the main flow conduit is connected in a flow path of a spray arm conduit fed by a circulating pump.

13. A washing device comprising:

a main flow conduit that is vertically disposed in an operating position of the washing device;

a washing tub and a plurality of housing walls surrounding the washing tub; and an apparatus for preventing foam or air bubbles from accumulating in a measuring zone of a turbidity sensor connected in a wash-water circuit of, the washing device, the apparatus comprising:

a bypass conduit connected to the main flow conduit, the bypass conduit including:

a first conduit section branching off from the main flow conduit at a branching off location;

a second conduit section leading back into the main flow conduit at a junction vertically above the branching off location; and an enlarged region of reduced flow velocity connected between the first and second conduit sections and providing the measuring zone of the turbidity sensor, the enlarged region including an abrupt enlargement and an abrupt narrowing of the bypass conduit forming a curved baffle and a downward-facing bulbous protuberance opposite the baffle so as to form a backflow region, the measuring zone being disposed in the backflow region in the bulbous protuberance;

wherein:

the turbidity sensor is connected in a wash-water circuit of the washing device, the plurality of housing walls including a first side wall disposed laterally outward from the washing tub; and the main flow conduit is disposed between the first side wall and the washing tub.

14. The device as recited in claim 12 wherein:

the turbidity sensor is connected in a wash-water circuit of a dishwasher including a washing tub surrounded by a plurality of housing walls and configured to wash dishes; and the main flow conduit is integrally formed as one piece with the spray arm conduit.

15. The device as recited in claim 13 wherein the main flow conduit is disposed at least 40 cm above the circulating pump.

16. The device as recited in claim 14 wherein the main flow conduit is disposed at least 40 cm above the circulating pump.

17. The device as recited in claim 1 wherein the curved baffle has a substantially circular shape.

18. The device as recited in claim 13 wherein a portion of the abrupt enlargement is downwardly, relative to a direction of gravity, inclined with respect to a horizontal plane in a direction of backflow.

19. The device as recited in claim 1 wherein the device is a dishwasher or a washing machine.

20. The device as recited in claim 13 wherein the device is a dishwasher or a washing machine.

* * * * *